(12) United States Patent
Bellussi et al.

(10) Patent No.: US 7,176,342 B2
(45) Date of Patent: Feb. 13, 2007

(54) METHOD FOR THE PREPARATION OF HYDROGENATED HYDROCARBONS

(75) Inventors: Giuseppe Bellussi, Piacenza (IT); Alberto DelBianco, Magenta (IT); Luigina Maria Flora Sabatino, San Donato Milanese (IT); Roberto Zennaro, Venice (IT); Mario Molinari, Milan (IT)

(73) Assignee: Enitecnologie S.p.A., Milan (IT)

( * ) Notice: Subject to any disclaimer, the term of this patent is extended or adjusted under 35 U.S.C. 154(b) by 84 days.

(21) Appl. No.: 10/110,782

(22) PCT Filed: Jan. 25, 2001

(86) PCT No.: PCT/EP01/00826

§ 371 (c)(1),
(2), (4) Date: Apr. 29, 2002

(87) PCT Pub. No.: WO01/56957

PCT Pub. Date: Aug. 9, 2001

(65) Prior Publication Data

US 2004/0015025 A1   Jan. 22, 2004

(30) Foreign Application Priority Data

Feb. 3, 2000   (IT) ............... MI2000A0166

(51) Int. Cl.
*C07C 2/00* (2006.01)

(52) U.S. Cl. ............... 585/943; 585/254; 585/310

(58) Field of Classification Search ............... 585/254, 585/310, 943
See application file for complete search history.

(56) References Cited

U.S. PATENT DOCUMENTS

| | | | | |
|---|---|---|---|---|
| 4,533,780 A | * | 8/1985 | Maffia | 585/330 |
| 4,599,474 A | * | 7/1986 | Devries et al. | 585/415 |
| 5,288,935 A | * | 2/1994 | Alario et al. | 585/322 |
| 5,414,176 A | * | 5/1995 | Amariglio et al. | 585/500 |
| 5,932,090 A | | 8/1999 | Marchionna et al. | |
| 6,239,057 B1 | * | 5/2001 | Ichikawa et al. | 502/66 |

FOREIGN PATENT DOCUMENTS

| | | | |
|---|---|---|---|
| EP | 192289 A2 | * | 8/1986 |
| EP | 0 858 987 | | 8/1998 |
| GB | 2191212 A | * | 12/1987 |
| WO | 92 01656 | | 2/1992 |
| WO | WO 9903949 A1 | * | 1/1999 |

OTHER PUBLICATIONS

U.S. Appl. No. 10/188,785, filed Jul. 5, 2002, Delbianco et al.

* cited by examiner

*Primary Examiner*—Thuan Dinh Dang
(74) *Attorney, Agent, or Firm*—Oblon, Spivak, McClelland, Maier & Neustadt, P.C.

(57) ABSTRACT

A method for the preparation of hydrogenated hydrocarbons comprising a preliminary treatment of natural gas with a catalyst at a high temperature and the subsequent hydrogenation of the mixture of cyclic and/or aromatic hydrocarbons formed.

17 Claims, 3 Drawing Sheets

PROCESS SCHEME FOR THE PREPARATION OF HYDROGENATED HYDROCARBONS.

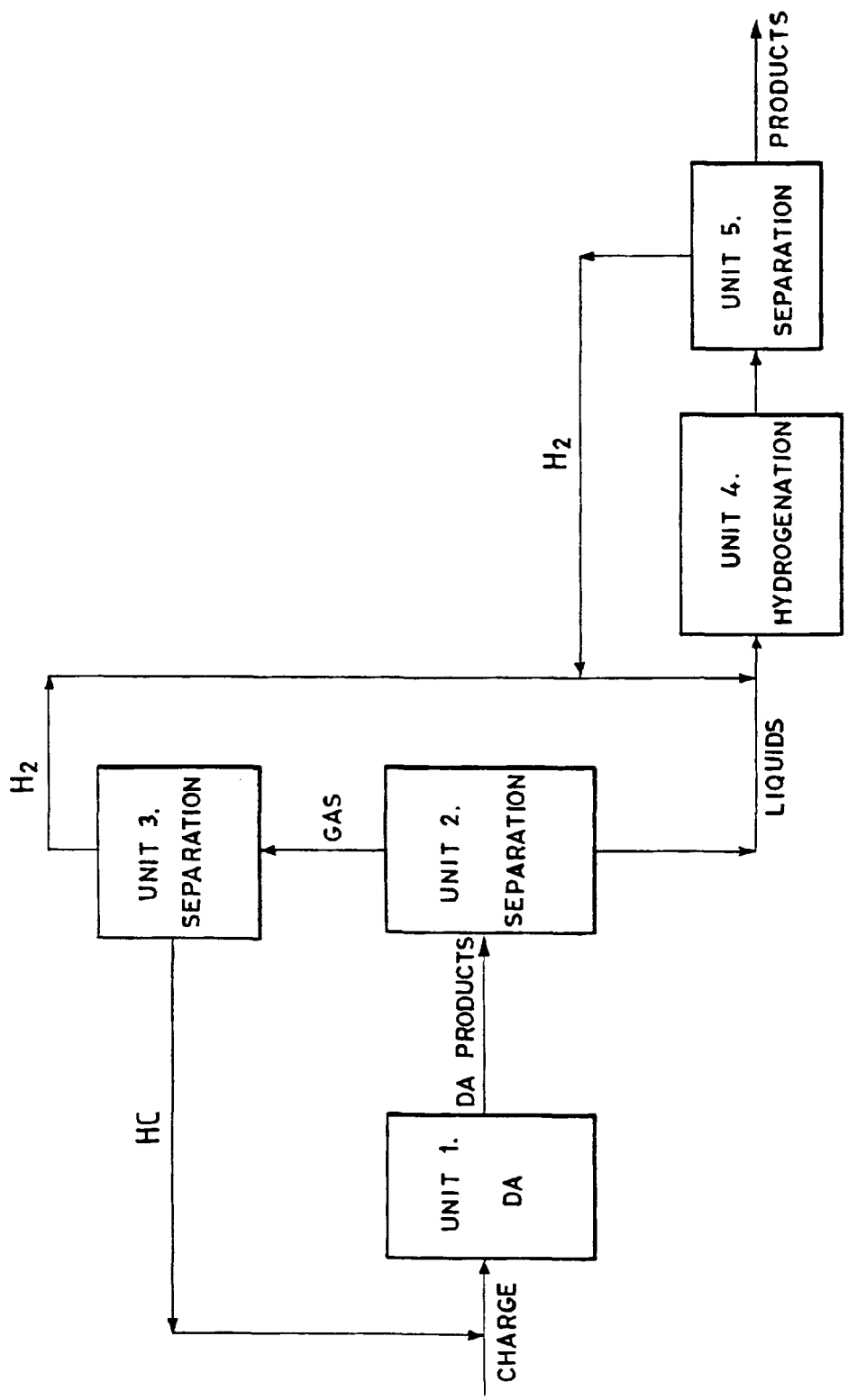

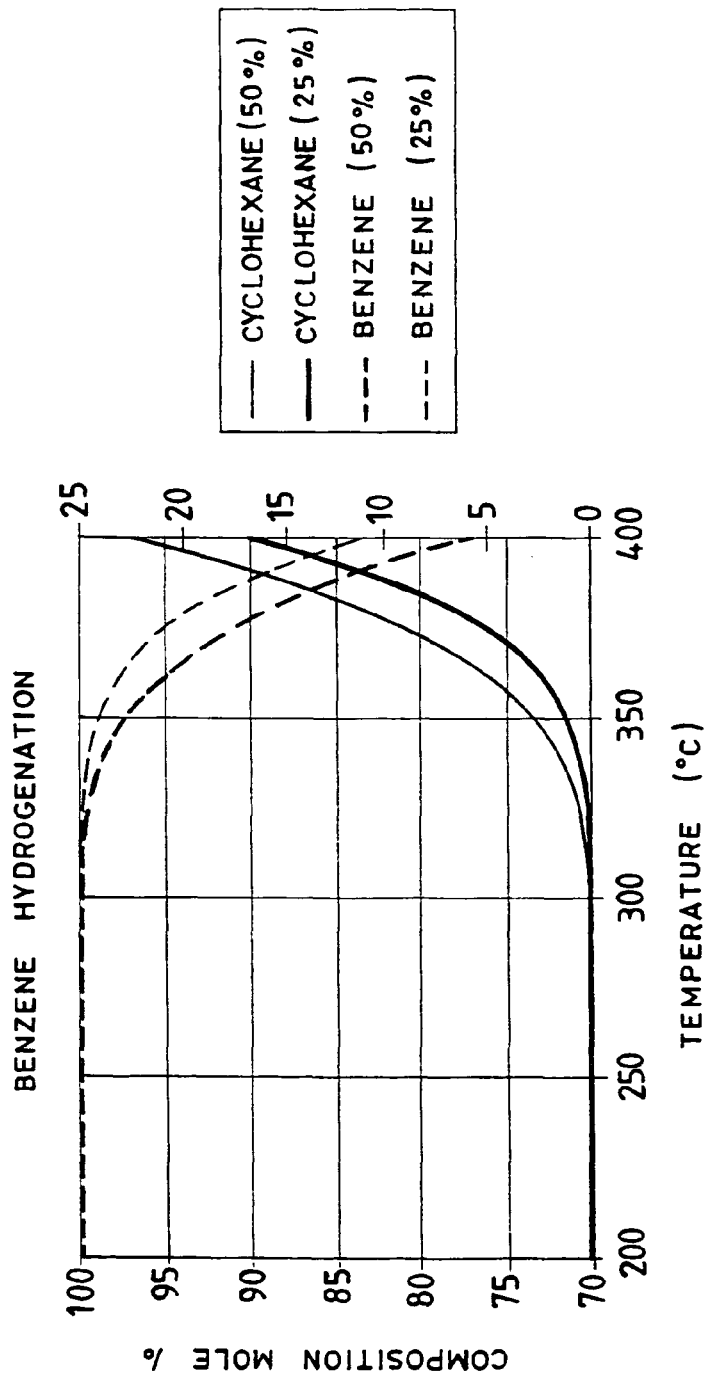

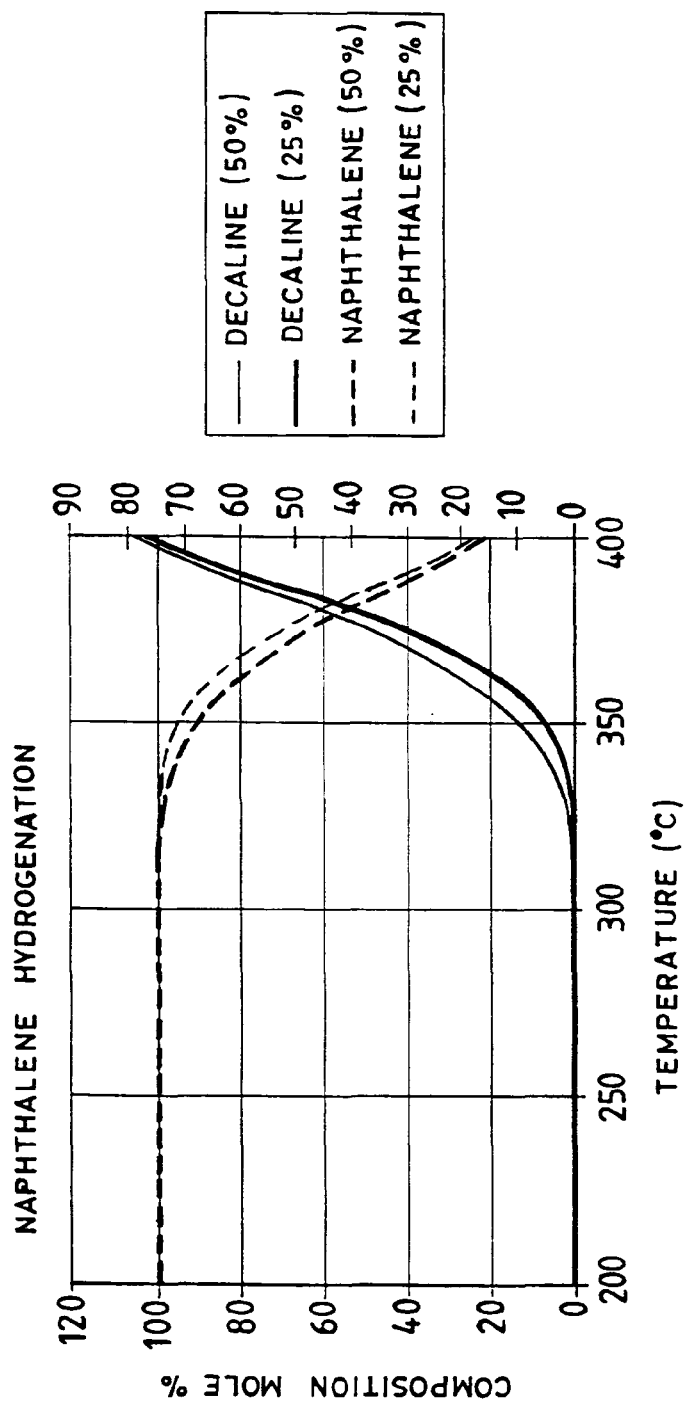

METHOD FOR THE PREPARATION OF HYDROGENATED HYDROCARBONS

The present invention relates to a method for the preparation of hydrogenated hydrocarbons, consisting in treating natural gas, at a high temperature, with a suitable catalyst in order to prepare a mixture of higher hydrocarbons basically consisting of cyclic and/or aromatic hydrocarbons and subjecting the mixture thus obtained to hydrogenation.

This process is particularly useful for the conversion of natural gas in the case of oil fields with associated gas or gas fields near oil fields for the collection, separation and transportation of the product.

The same process has proved to be particularly advantageous for the recovery and use of so-called associated gas, of which it has therefore become an interesting exploitation method: in the following description, the details of the process according to the present invention are specified with reference to associated gas, even though the process itself is of a completely general nature. The following definitions and specific operating results, should therefore not be considered as restricting the process according to the present invention.

It is known that the term associated gas refers to the gas present in a crude-oil field both as gas phase in equilibrium with the oil phase, and also dissolved in the crude-oil under field conditions. On a world-wide scale, it forms about 30% of natural gas reserves.

Depending on the field, the quantity of associated gas can vary from a few cubic meters to over 150 $m_3$ of gas per $m^3$ of oil.

Also from a compositional point of view, there are significant differences with respect to the relative ratio between hydrocarbons and the presence of acid gases ($H_2S$ and $CO_2$) or nitrogen.

The production of associated gas is inevitably connected to the production of oil which in most cases forms the main product, so that, in relation to the geographical area in which it is extracted, it can be recovered and transported, re-injected into the well or burnt in a torch (gas flaring).

It is also known, on the other hand, that refinery and chemical plant activities comprise the transformation of relatively low value hydrocarbons into higher quality hydrocarbon streams or to actual chemical products. Methane, for example, the simplest of saturated hydrocarbons, often appears in large quantities as by-product mixed with other hydrocarbons with a higher molecular weight, or as gas component at the outlet of process units. Although methane is actually used in various chemical reactions (such as the production of methanol and formaldehyde), it is not as useful as hydrocarbons with a higher molecular weight: for this reason, process streams containing methane are normally burnt as fuels.

Methane however is also the main component of natural gas which consists of a mixture of gaseous hydrocarbons basically comprising methane mixed with ethane, propane, butane and traces of other higher hydrocarbons.

Natural gas can also be processed and converted into hydrocarbons liquid at room temperature to enable it to be used as fuel.

As of today, the industrially developed methods for effecting this transformation pass through the production of syngas, which can subsequently be converted to methanol or waxes via Fischer-Tropsch synthesis (indirect conversion).

As far as direct conversion is concerned, i.e. the transformation of natural gas to liquid hydrocarbons in a single step, various methods have been proposed among which oxidative coupling (i.e. a pyrolysis carried out in the presence of oxygen on suitable catalysts) and non-oxidative pyrolysis which leads to the production of light olefins (ethylene and propylene) and aromatics (BTX, naphthalene, etc.), and hydrogen.

The production of higher hydrocarbons from methane becomes significant at high temperatures and whenever the conversion is carried out in the presence of a catalyst which can guarantee high synthesis rates of the higher hydrocarbons also under thermodynamically unfavourable conditions: the presence of a suitable catalyst can also significantly influence the distribution of the products in the end mixture.

For example, European patent application 192.289 describes the direct conversion of natural gas to aromatic hydrocarbons, at high temperatures, on a catalyst based on alkaline silicate and also comprising aluminum and/or gallium.

International patent application WO-A-92/01656 describes the same conversion in the presence of a transition metal supported on a refractory material substantially consisting of a metal oxide, at a temperature up to 300° C.

European patent application 858,987, refers, in turn, to a process for the conversion of a mixture of light hydrocarbons, in the gas state under normal temperature and pressure conditions and containing methane, to higher hydrocarbons, liquid under normal temperature and pressure conditions, said process comprising an absorption step of the mixture in question on a supported metallic catalyst comprising a metal or combination of metals at least one of which belonging to Group VIII of the Periodic System, followed by a desorption phase, the first step being effected at a temperature not lower than 300° C.

Of particular interest for the conversion of methane to aromatic compounds, is the catalyst consisting of molybdenum supported on H-ZSM-5 zeolite, as also described in Journal of Catalysis 181, 175–188 (1999).

The methods for the production of higher hydrocarbons to which the above state of the art relates, or the disclosure for effecting said methods, according to said state of the art, all seem to stress the importance of the concentration of methane in the gas mixture to be fed to the high temperature treatment, and practically predict the possibility of industrial advantages in the conversion of methane alone. Due to the necessity of starting from mixtures containing it in different percentages, this would require costly and difficult pretreatment processes for the separation and removal of the other constituents of the mixture of interest and the methods themselves would also be difficult to apply on an industrial scale, in spite of the use of catalytic systems of varying compositions.

The Applicant has now found, and this is among the objectives of the present invention, that it is possible to prepare mixtures of higher hydrocarbons by directly subjecting associated gas, already in its formation site and without the necessity of previously enriching the relative mixture in methane gas, to a high temperature thermal treatment in order to produce aromatic hydrocarbons having from 1 to 3 condensed rings and/or variously substituted with alkyl groups and hydrogen which can be recovered with specific storage tanks.

The aromatic products can be initially mixed with the oil produced contemporaneously and transported. When the quantity of hydrogen stored is sufficient, it can be subsequently used to hydrogenate part or all of the aromatic hydrocarbon in order to produce naphthene compounds with a high hydrogen/carbon ratio. In this way the oil produced can be enriched with fractions of distillates for the production of fuels and/or intermediates for the petrochemical industry.

On the whole, the process proposed allows streams of natural gas, which would otherwise be unusable or difficult to transport as gas, to be converted into liquid hydrocarbon products compatible with the oil itself. The possibility of transforming associated gas into liquid hydrocarbons also enables oil fields to be exploited, which for logistic reasons or due to environmental regulations (gas flaring restrictions) could not be put into production owing to the impossibility of treating the gas component.

In this way, a mixture which is normally sent for combustion is converted into products of industrial interest, obtaining at the same time, specific exploitation of the mixture itself.

In particular, an object of the present invention relates to a method for the preparation of hydrogenated hydrocarbons according to which a mixture of cyclic and/or aromatic hydrocarbons is prepared by sending associated gas, selected from those defined above, through a catalytic composition at a temperature not lower than 350° C. and at a pressure of not less than 0.2 bars, and the products thus obtained are immediately subjected to hydrogenation, according to techniques well known to experts in the field, using suitable catalysts and maintaining the reaction temperature at about 250–300° C.

Catalysts suitable for the preliminary conversion of associated gas into liquid products are all those mentioned in the state of the art: it is therefore possible to use the supported catalyst described in European patent application 858,987 mentioned above, which consists of one or more metals selected from those of Group VIII of the Periodic System deposited on a carrier consisting of an oxide: particular emphasis is laid on a nickel/copper mixture.

The catalytic composition described in International patent application 99/03949, consisting of a mixture comprising a zeolite and a zinc aluminate previously treated with a reducing gas at a high temperature, can also be used.

From a completely general point of view, the following compositions can be used in the process according to the present invention:

a catalyst consisting of a zeolite and one or more of the following components: oxides of alkaline and earth alkaline metals/oxides of group IIIA/metals of group IVB, VB, VIB, VIIB, VIIIB, IB, IIB, IIIB and a ligand consisting of refractory oxides or their mixtures selected from $SiO_2$, $Al_2O_3$, $ZrO_2$, $TiO_2$, MgO.

The zeolite is selected from the MFI, MTT, TON, NES, MEL, MTW, MWW (ERB-1), BEA, FER, MOR, FAU, ERS, OFF structural types.

Zeolites selected from those indicated above, in which part of the silicon has been substituted with Ti.

Zeolites selected from those indicated above, in which part of all of the Al has been substituted with B, Fe, Ga, V, Cr.

Zeolites impregnated or exchanged with metals of groups IVB, VB, VIB, VIIB, VIIIB, IB, IIB, IIB with a weight percentage ranging from 0.01–30%.

Zeolites exchanged with a metal of Groups VIII, IB, IIB, impregnated with V, Mo, W, treated with a promoter such as Ru, Rh, Pd, Pt in a quantity ranging from 0.001–5% preferably between 0.01–2% by weight.

A catalyst consisting of one or more of the components indicated above impregnated with an alkaline metal.

The metal or metals can be deposited on the zeolite by ion exchange in solution, ion exchange in the solid state, by impregnation, by precipitation under suitable conditions. Several metals can be deposited in a single step or following a multi-step procedure. In a multi-step preparation the intermediates can be dried only or dried and calcined. The end catalyst is dried and calcined in the presence of air.

According to a preferred embodiment, the process according to the present invention comprises a first conversion step of the associated gas into liquid products by means of dehydro-aromatization with the formation of aromatic products (mainly benzene and naphthalene) followed by hydrogenation which allows the production of naphthene products.

The conversion of the gas can be effected at a temperature value of 350–800° C., depending on the composition of the gas and catalyst selected, at a pressure ranging from 0.2–5 bars and a GHSV of 500–50000 $h^{-1}$.

The method according to the present invention is now described in further detail by means of a few examples which are naturally only illustrative and do not limit the scope of the invention. In these examples reference is made to process units and procedures well known to experts in the field.

The process for the preparation of hydrogenated hydrocarbons according to the present invention can be illustrated by means of the block scheme of FIG. 1. This consists of the following units:

1. Dehydro-aromatization unit of methane or its mixtures.
2. Gas-liquid separation unit ($H_2$+light hydrocarbons-aromatic hydrocarbons).
3. Separation unit of $H_2$ from light hydrocarbons. The hydrogen thus separated is used for the hydrogenation of aromatics whereas the light hydrocarbons are recycled and together with methane or its mixtures form the dehydro-aromatization charge.
4. Hydrogenation unit of aromatics using the hydrogen produced in the dehydro-aromatization unit.
5. Separation unit of hydrogen from naphthene compounds. The hydrogen recovered is recycled to the hydrogenation unit.

EXAMPLE

General procedure for the dehydro-aromatization of pure methane or its mixtures.

A suitable quantity of catalyst is charged into the reactor which is inserted into a furnace. The catalyst is then activated at a temperature selected within the range of 350–700° C., while a stream of gas is emitted (duration 15–120 minutes). The activation can be carried out with an inert gas (He, N, Ar), with a reducing or oxidizing agent. After treating the catalyst in an oxidizing or reducing environment, the stream is substituted with an inert gas (15–20 minutes). When the reaction temperature has been reached, the reagent mixture is sent onto the catalyst.

Data are provided hereunder relating to the equilibrium composition for the transformation of methane (Table 1), of a mixture consisting of methane/ethane (Table 2) and associated gas (Table 3) to higher hydrocarbons.

TABLE 1

| | Conversion off methane (calculated data). % Selectivity[1] | | | | | | |
|---|---|---|---|---|---|---|---|
| T° C. | 500 | 550 | 600 | 650 | 700 | 750 | 800 |
| Benzene | 34.20 | 34.76 | 34.91 | 34.45 | 33.98 | 33.60 | 33.05 |
| Naphthalene | 54.50 | 56.76 | 58.00 | 58.59 | 59.28 | 60.27 | 61.02 |
| Ethylene | 0.34 | 0.50 | 0.69 | 0.91 | 1.15 | 1.42 | 1.69 |
| Other prod. | 10.95 | 7.96 | 6.40 | 6.06 | 5.58 | 4.41 | 4.24 |
| | | | Methane conversion | | | | |
| | 2.00 | 3.40 | 5.50 | 8.50 | 12.50 | 17.50 | 23.60 |

[1]Selectivity referring to the C moles

TABLE 2 conversion of the mixture ethane 10% and
methane 90% (calculated data)
% Selectivity[1]

| T° C. | 500 | 550 | 600 | 650 | 700 | 750 | 800 |
|---|---|---|---|---|---|---|---|
| Benzene | 22.52 | 24.30 | 27.66 | 29.22 | 30.22 | 30.66 | 30.82 |
| Naphthalene | 73.43 | 66.42 | 66.84 | 65.15 | 64.14 | 63.99 | 64.20 |
| Ethylene | 0.11 | 0.21 | 0.38 | 0.59 | 0.84 | 1.12 | 1.42 |
| Other prod. | 3.93 | 9.07 | 5.12 | 5.04 | 4.80 | 4.23 | 3.57 |
| Methane-ethane conversion (% C) | | | | | | | |
| | 7.17 | 8.98 | 10.61 | 13.42 | 17.15 | 21.88 | 27.61 |

[1]Selectivity referring to the C moles

On comparing the data of Table 1 and Table 2, it can be seen that in the presence of ethane the conversion, expressed as percentage of C moles converted, increases and the selectivity to aromatics increases with a condensation degree higher than benzene. The presence of other hydrocarbons in addition to ethane causes a further increase in the conversion of the gas. Furthermore, in the presence of $C_2$, $C_3$, $C_4$ there is a significant conversion even at low temperatures at which methane does not pyrolyze.

The data indicated in Table 3 were obtained for the following composition: methane 69.4%, ethane 7.9%, propane 4.5%, butane 4.5%.

TABLE 3 conversion of associated gas (calculated data)
% Selectivity[1]

| T° C. | 500 | 550 | 600 | 650 | 700 | 750 | 800 |
|---|---|---|---|---|---|---|---|
| Benzene | 14.99 | 18.07 | 20.81 | 23.10 | 25.02 | 26.30 | 27.04 |
| Naphthalene | 73.03 | 76.18 | 73.73 | 71.49 | 70.25 | 68.91 | 68.42 |
| Ethylene | 0.05 | 0.10 | 0.19 | 0.34 | 0.53 | 0.76 | 1.02 |
| Other prod. | 6.94 | 5.65 | 5.27 | 5.07 | 4.21 | 4.04 | 3.52 |
| Ethane conversion, $C_3$, and $C_4$ (% C) | | | | | | | |
| | 17.90 | 19.01 | 20.80 | 23.37 | 26.71 | 31.09 | 36.32 |

[1]Selectivity referring to the C moles

Preparation of the Catalyst

For the catalytic conversion of methane to higher hydrocarbons under non-oxidizing conditions, a sample consisting of Mo—ZSM-5 was used, having the following composition: molar ratio $SiO_2/Al_2O_3$=58.6, Mo (w/w %)=1.90. The zeolite was prepared according what is described in U.S. Pat. No. 3,702,886, the Molybdenum was introduced by impregnation using a solution of ammonium heptamolybdate.

Determination of the Catalytic Activity

Conversion of Methane

For the determination of the catalytic activity, a quartz tubular reactor was used, having an internal diameter of 20 mm, kept in an electric oven in the constant temperature zone. In the initial phase, the reactor was heated with a rise of 10° C./min up to the operating temperature, 700° C.; it was maintained for 30 minutes in a stream of air (100 ml/min) and then for 10 minutes in Argon (100 ml/min).

After this initial phase, the reactor was fed with pure methane with a GHSV equal to 1500 ml/(g h).

The characterization of the products was effected with an HP 5890 gas-chromatograph using both a TCD and FID as detector.

The reaction compounds initially consisted of CO and $CO_2$; approximately 60 minutes after the beginning of the feeding the presence of CO and $CO_2$ was no longer registered and, at the same time, the products appeared. The production of the products remained constant for about 70 hours during which the stream of methane remained uninterrupted.

The conversion was calculated from the ratio: $(CH_{4in}-CH_{4out})/CH_{4in}$. The selectivity was calculated considering the ratio of the number of carbon atoms contained in the single molecule of the product with respect to the total carbon converted. Conversion and selectivity are indicated in Table 4.

The catalytic performances can be at least partially re-established (oxidation of the carbonaceous and polycondensed residues) using a regeneration process which comprises a cooling phase to 100° C. in argon and a heating phase (5° C./min) in air.

TABLE 4

Conversion and selectivity for the
dehydroaromatization of methane.

| Product | Selectivity % |
|---|---|
| $CH_4$ conv. % | 10 |
| Ethylene | 2.4 |
| Ethane | 1.3 |
| Benzene | 66.7 |
| Toluene | 3.2 |
| Naphthalene | 26.4 |

Conversion of Natural Gas

A gas having the following composition was used: Methane: 69.4°, ethane 7.9%, propane 4.5%o, butane 4.5%.

The experimental conditions relating to the pretreatment of the catalyst, space velocity and analysis method are described in the paragraph relating to the conversion of methane. The reaction temperature was varied between 550–700° C.

Table 5 indicates the data relating to $C_1$–$C_4$ conversion and the selectivity towards aromatics and other products.

TABLE 5

Conversion and selectivity for the
dehydroaromatization of natural gas.

| | Selectivity % | | |
|---|---|---|---|
| Product | 550° C. | 600° C. | 700° C. |
| $C_1$–$C_4$ conv. % | 16 | 18.5 | 24.3 |
| Aromatics | 90.7 | 89.6 | 89.8 |
| Ethylene | 1.05 | 1.2 | 2.4 |
| Other products | 8.25 | 9.2 | 7.8 |

Separation and Hydrogenation of Aromatic Compounds.

Separation

Aromatics can be easily separated from methane and other light gases due to the considerable difference in relative volatility. At room temperature it is possible to effect the separation by means of compression. As an alternative to compression, resort can be made to washing with a heavy hydrocarbon compound. In this case, the partial pressure in vapor phase of the benzene is reduced as a result of the decrease in the molar fraction in liquid phase due to the addition of the non-volatile heavy product. Using $C_{30}$ as absorbing liquid and simulating an absorption column with 10 theoretical steps, a 95% recovery of the benzene fed is obtained.

Hydrogenation

The hydrogenation can be carried out on catalysts consisting of supported metals of Group VIII (Pt, Pd, Ru, Ni). Using noble metals supported on zeolites, the hydrogenation, effected at 260–315° C., at a pressure equal to 4.2 MPa, LHSV 3–4 $h^{-1}$, proves to be 95%.

The hydrogenation can be carried out by feeding hydrogen to the mixture produced during the preliminary high temperature treatment; or, according to a preferred embodiment, the same mixture is removed as it is formed, to be subsequently subjected to hydrogenation on the part of the same hydrogen gas produced and accumulated during the same thermal treatment.

Data are provided hereunder relating to the equilibrium composition for the hydrogenation of benzene (Table 6, FIG. 2) and naphthalene (Table 6, FIG. 3) with respect to the transformation of 1 Kmol with a hydrogen excess of 25% or 50% at 42 Bars.

TABLE 6

Equilibrium composition for the hydrogenation of 1 Kmol of benzene and naphthalene.
Moles %

| T° C. | 200 | 220 | 240 | 260 | 280 | 300 | 320 | 340 | 360 | 400 |
|---|---|---|---|---|---|---|---|---|---|---|
| Benzene ($H_2$ 25%) | 5.39E−6 | 4.98E−5 | 3.90E−4 | 2.63E−3 | 1.55E−2 | 8.07E−2 | 3.71E−1 | 1.46 | 4.58 | 2.27 |
| Benzene ($H_2$ 50%) | 1.97E−6 | 1.82E−5 | 1.42E−4 | 9.58E−4 | 5.65E−3 | 2.96E−2 | 1.39E−1 | 5.82E−1 | 2.15 | 1.68 |
| Naphthalene ($H_2$ 25%) | 2.00E−8 | 6.42E−7 | 1.59E−5 | 3.13E−4 | 5.01E−3 | 6.62E−2 | 7.01E−1 | 4.77 | 1.79 | 7.92 |
| Naphthalene ($H_2$ 50%) | 5.71E−9 | 1.83E−7 | 4.53E−6 | 8.91E−5 | 1.43E−3 | 1.90E−2 | 2.12E−1 | 1.92 | 1.16 | 7.67E+1 |

Hydrogenation of Aromatic Compounds

The aromatics essentially consisting of benzene, toluene, naphthalene and methyl-naphthalenes, after separation from the lower hydrocarbons, are hydrogenated to naphthene products.

The hydrogenation was carried out in a fixed bed reactor under the following conditions:

P=62 bars, T=315° C.; $H_2$/aromatics=712 $Nm^3/m^3$, LHSV=1 $h^{-1}$, catalyst=Y zeolite impregnated with Pt (0.5 Kg/l).

Under these conditions the conversion to hydrogenated products is 98%.

The invention claimed is:

1. A method for the preparation of hydrogenated hydrocarbons consisting of a preliminary treatment of natural gas with a catalyst carried out at a temperature between 350 and 750° C. and the subsequent hydrogenation of the mixture of cyclic and/or aromatic hydrocarbons formed carried out at a temperature between 260 and 315° C. with a catalyst comprising a metal belonging to group VIII of the Periodic System duly supported.

2. The method for the preparation of hydrogenated hydrocarbons according to claim 1, wherein the gas fed to the preliminary treatment is associated gas.

3. The method for the preparation of hydrogenated hydrocarbons according to claim 1, wherein the preliminary treatment is carried out by sending the natural gas through the catalytic composition at a pressure not less than 0.2 bars.

4. The method for the preparation of hydrogenated hydrocarbons according to claim 1, wherein the preliminary treatment is effected in a fixed bed reactor.

5. The method for the preparation of hydrogenated hydrocarbons according to claim 1, wherein the preliminary treatment is effected in a fluid bed reactor.

6. The method for the preparation of hydrogenated hydrocarbons according to claim 1, wherein the preliminary treatment is effected at a pressure from 0.2 to 5 bars.

7. The method for the preparation of hydrogenated hydrocarbons according to claim 1, wherein the preliminary treatment is carried out at a GHSV ranging from 500 to 50000 $h^{-1}$.

8. The method for the preparation of hydrogenated hydrocarbons according to claim 2, wherein the preliminary treatment is carried out in the presence of a catalytic composition comprising one or more metals selected from those of Group VIII of the Periodic System deposited on a carrier comprising an oxide.

9. The method according to claim 8, wherein the metals are a nickel/copper mixture.

10. The method for preparation of hydrogenated hydrocarbons according to claim 2, wherein the preliminary treatment is carried out in the presence of a catalytic composition comprising a mixture comprising a zeolite and a zinc aluminate previously treated with a reducing gas at a high temperature.

11. The method for the preparation of hydrogenated hydrocarbons according to claim 2, wherein the preliminary treatment is carried out in the presence of a catalytic composition comprising a zeolite and one or more of the following components: oxides of alkaline and earth alkaline metals/oxides of Group IIIA/metals of group IVB, VB, VIB, VIIB, VIIIB, IB, IIB, IIIB and a ligand consisting of refractory oxides or their mixtures selected from $SiO_2$, $Al_2O_3$, $ZrO_2$, $TiO_2$, MgO.

12. The method according to claim 11, wherein the zeolite is selected from MFI, MTT, TON, NES, MEL, MTW, MWW (ERB-1), BEA, FER, MOR, FAU, ERS, OFF structural types.

13. The method according to claim 11, wherein, in the zeolites, part of the silicon is substituted with Ti.

14. The method according to claim 11, wherein, in the zeolites, part of all of the Al is substituted with B, Fe, Ga, V, Cr.

15. The method of claim 2, wherein the preliminary treatment is the conversion of the associated gas into one or more liquid products.

16. The method of claim 6, wherein the preliminary treatment is the conversion of the associated gas into one or more liquid products.

17. A method for the preparation of hydrogenated hydrocarbons comprising a preliminary treatment of natural gas with a catalyst carried out at a temperature between 350 and 800° C. and, immediately after said preliminary treatment, the subsequent hydrogenation of the mixture of cyclic and/or aromatic hydrocarbons formed carried out at a temperature between 260 and 315° C. with a catalyst comprising a metal belonging to group VIII of the Periodic System duly supported.

* * * * *